United States Patent [19]

Kwak et al.

[11] Patent Number: 5,145,669
[45] Date of Patent: * Sep. 8, 1992

[54] SUNSCREEN COMPOSITION

[75] Inventors: Yoon T, Kwak, Brooklyn, N.Y.; Stephen L. Kopolow, Plainsboro, N.J.; Michael W. Helioff, Westfield, N.J.; Mohammed Tazi, Wayne, N.J.

[73] Assignee: ISP Investments Inc., Wilmington, Del.

[*] Notice: The portion of the term of this patent subsequent to Jul. 23, 2008 has been disclaimed.

[21] Appl. No.: 732,847

[22] Filed: Jul. 19, 1991

Related U.S. Application Data

[63] Continuation-in-part of Ser. No. 564,920, Aug. 9, 1990.

[51] Int. Cl.$^5$ .................. C08F 255/08; C08F 261/06; C08F 267/04; C08F 222/06; C08F 216/12; A61K 7/42
[52] U.S. Cl. ..................................... 525/313; 424/59; 526/271; 526/332; 526/348.3; 525/313
[58] Field of Search .......................... 526/271

[56] References Cited

U.S. PATENT DOCUMENTS 4,370,454  1/1983  Messmer eet al. .................. 526/88
5,034,486  7/1991  Tzai et al. .......................... 526/271

Primary Examiner—Joseph L. Schofer
Assistant Examiner—Wu C. Cheng
Attorney, Agent, or Firm—Marilyn J. Maue; Walter Katz; Joshua J. Ward

[57] ABSTRACT

What is provided herein is a sunscreen composition consisting essentially of a crosslinked, neutralized terpolymer of maleic anhydride, a $C_1$–$C_5$ alkyl vinyl ether and a $C_{12}$–$C_{14}$ alpha-olefin monomer as a thickener; water; an ultraviolet sunscreening agent; and an emulsifier. In the preferred form of the invention, the monomers are present in a molar ratio of about 1:0.90–0.99:0.01–0.10, respectively, and are crosslinked with about 2–8 wt. % of a crosslinking agent based on the total weight of the monomers. Suitably, the crosslinked terpolymer is neutralized to increase water solubility.

14 Claims, No Drawings

SUNSCREEN COMPOSITION

CROSS-REFERENCE TO RELATED PATENT APPLICATIONS

This application is a continuation-in-part of pending U.S. patent application, Ser. No. 564,920, filed Aug. 9, 1990, and assigned to the same assignee as herein.

BACKGROUND OF THE INVENTION

1. Field of the Invention

This invention relates to personal care compositions, and, more particularly, to sunscreen products in which the active component is trapped within a gel material in a thickened condition.

2. Description of the Prior Art

In recent years, increased awareness of the porentially harmful effects of solar radiation has led to rapid growth in the use of sunscreen products. As sunscreens are usually applied prior to activities such as bathing or sports, the consumer requires a product that will remain effective after exposure to water and/or perspiration.

The use of water-insoluble active sunscreen ingredients is usually insufficient to provide adequate water resistance. A thickener also is required in such formulations. However, an effective method of accomplishing water resistance or waterproofing of a sunscreen formula is to employ a water-insoluble substantive film forming resin. A Carbomer resin can provide thickening action. Typical materials for waterproofing sunscreen formulations are two resins which are copolymers of vinylpyrrolidone and long chain alkanes, $C_{16}$ and $C_{20}$. They are oil-soluble film forming polymers which have been used for some time by the cosmetics industry. However, it is desired to provide new and improved resins which can provide the thickener property in sunscreen formulation, and contribute to its waterproofing characteristics.

SUMMARY OF THE INVENTION

What is provided herein is a sunscreen composition consisting essentially of a crosslinked, neutralized terpolymer of maleic anhydride, a $C_1$–$C_5$ alkyl vinyl ether and a $C_{12}$–$C_{14}$ alpha-olefin monomer as a thickener; water; an ultraviolet sunscreening agent; and an emulsifier. In the preferred form of the invention, the monomers are present in a molar ratio of about 1:0.90–0.99:0.01–0.10, respectively, and are crosslinked with about 2–8 wt. % of a crosslinking agent based on the total weight of the monomers. Suitably, the crosslinked terpolymer are neutralized to increase their water solubility.

The sunscreen composition preferably comprises about 0.5–8 wt. % of the crosslinked, neutralized terpolymer; about 1–7 wt. % of the ultraviolet sunscreening agent; about 1–5 wt. % of an emulsifier; and, preferably, about 0.1–5 wt. % of an emollient; about 0.1–5 wt. % of a secondary waterproofing agent; about 0.5–2 wt. % of a germacide; and about 0.1–0.5 wt. % of a fragrance; the rest being water, usually in the amount of about 70–95 wt. %.

The crosslinked, neutralized terpolymer component of the sunscreen composition of the invention provides an effective thickener for the composition and enhanced waterproofing properties.

DETAILED DESCRIPTION OF THE INVENTION

The crosslinked, neutralized terpolymer comprises maleic anhydride, a $C_1$–$C_5$ alkyl vinyl ether and a $C_{12}$–$C_{14}$ alpha-olefin, suitably in a molar ratio of about 1:0.90–0.99:0.01–0.10, preferably about 1:0.94–0.96:0.04–0.06, respectively, which is crosslinked with about 2–8 wt. % of total monomers in the terpolymer of a crosslinking agent, and neutralized with sufficient base to provide water solubility, e.g. about 2.6 g. of a 10% NaOH solution per 1 g. of the crosslinked terpolymer.

Representative $C_1$–$C_5$ alkyl vinyl ethers include methyl vinyl ether, propyl vinyl ether and butyl vinyl ether. Suitable $C_{12}$–$C_{14}$ alpha-olefins include straight chain unsaturated hydrocarbons such as dodecene and tetradecene. Suitable crosslinking agents include 1,7-octadiene, 1,9-decadiene, divinyl ethers and allyl carbohydrates.

These terpolymers are particularly characterized by a predetermined ratio between the hydrophobic straight chain unsaturated $C_{12}$–$C_{14}$ hydrocarbon component and the hydrophilic maleic anhydride component, which ratio affords a suitable hydrophilic-lipophilic balance (HLB) for the terpolymer and its crosslinked derivative The terpolymer is made by polymerizing the monomers, preferably in a mixed solvent comprising a cycloaliphatic hydrocarbon, such as cyclohexane, and an aliphatic carboxylic ester, such as ethyl acetate. In this process, a suitable reactor is provided with appropriate inlet tubes, agitation means, and heater and temperature control means. The reactor is first purged with nitrogen to remove air from the system. Generally three separate purges are employed, at about 3 bars pressure and about 40° C. The reactor is precharged with maleic anhydride and the crosslinking agent in a suitable solvent which may be an aromatic hydrocarbon such as benzene or toluene but is preferably a 50:50 mixture of cyclohexane and ethyl acetate.

The precharged reactor then is purged with nitrogen at about 58° C. and a free-radical polymerization initiator is introduced in three stages during the polymerization, generally at the beginning, after about 1½ hours and finally after about 3 hours, for a polymerization period of about 3 hours. Alternately, the initiator can be introduced in a continuous manner, e.g. as a solution in the reaction solvent Any suitable initiator known in the art may be used including but not limited to peroxides. Tertiary butyl or tertiary amylperoxy pivalate is preferred. The concentration of initiator may vary widely, although suitably the initiator comprises about 0.05 to 2% by weight of the maleic anhydride reactant.

Then, simultaneously with feeding of initiator, the alkyl vinyl ether and alpha-olefin monomers are introduced separately or together into the precharged reactor, and at a controlled rate, during the course of the polymerization.

Overall, the molar ratio of maleic anhydride to the combined alkyl vinyl ether and alpha-olefin monomers in the process is set at about less than 1:1. In practice, about a 10% excess of the alkyl vinyl ether over the 1:1 ratio is used to ensure complete conversion of the maleic anhydride to the terpolymer.

Of course, during the polymerization, the reaction mixture is agitated effectively, and, at the conclusion of the polymerization, the reaction product is held at the polymerization temperature for about 1½ hours. Then excess alkyl vinyl ether is vented and the product is discharged, filtered and the fine powders of the terpolymer is dried.

EXAMPLE 1

60.0 g. (0.612 mole) of maleic anhydride was precharged into a reactor with 4.78 g. (0.343 mole) of tetradecene, 4.78 g. (0.0434 mole) of 1,7-octadiene and 420 g. of a 50:50 mixture of cyclohexane and ethyl acetate. The reactor was purged with nitrogen and heated to 58° C. Then a mixture of 39.09 g. (50.88 ml., 0.365 mole) of methyl vinyl ether was admitted into the reactor slowly over a period of 3 hours. Simultaneously, three portions of 0.1 g. each (0.5% based on MA) of Lupersol 11 were admitted during the polymerization. After 3 hours, the reaction product was held at 58° C. for 1½ hours, cooled to room temperature, excess methyl vinyl ether vented and the product was discharged, filtered and dried to provide a fine, dry crosslinked terpolymer product.

The crosslinked terpolymer comprised a molar ratio of maleic anhydride to methyl vinyl ether to tetradecene (MA:MVE:TD) of about 1.0:0.96:0.04 and was crosslinked with 5.0% by weight of 1,7-octadiene based on the total weight of the terpolymer.

The crosslinked terpolymer, 1 g., was neutralized with 2.6 g. of a 10% NaOH solution to provide a water soluble crosslinked terpolymer.

The sunscreen composition of the invention suitably comprises:

| Component | Sunscreen Composition Wt. % Suitable | Preferred |
| --- | --- | --- |
| 1. Crosslinked, neutralized terpolymer of invention | 0.5-8 | 2.5 |
| 2. Ultraviolet sunscreening agent | 1-7 | 4.0 |
| 3. Emulsifier | 1-5 | 3.5 |
| 4. Emollient | 0.1-5 | 1.0 |
| 5. Waterproofing agent | 0.1-5 | 1.0 |
| Germacide | 0.5-2 | 1.0 |
| 7. Fragrance | 0.1-0.5 | 0.4 |
| 8. Water qs e.g. | 70-95 | 86.6 |

To prepare the composition, components 1-5 are heated to 80°-85° C.; the water component is heated separately to 80°-85° C.; the mixture of 1-5 is added to the water; components 6-7 are added at 35-40° C., and the mixture is cooled to room temperature.

These sunscreen compositions perform effectively in the usual tests for blockage of ultraviolet radiation.

While the invention has been described with particular reference to certain embodiments thereof, it will be understood that changes and modifications may be made which are within the skill of the art. Accordingly, it is intended to be bound only by the following claims, in which:

What is claimed is:

1. A thickened sunscreen composition having waterproofing properties consisting essentially of a crosslinked, neutralized terpolymer of maleic anhydride, a $C_1$–$C_5$ alkyl vinyl ether and a $C_{12}$–$C_{14}$ alpha-olefin in the molar ratio of about 1:0.90–0.99:0.01–0.10, an ultraviolet sunscreening agent, an emulsifier and water.

2. A sunscreen composition according to claim 1 wherein the monomers are present in the terpolymer in a molar ratio of about 1:0.94–0.96:0.04–0.06 respectively.

3. A sunscreen composition according to claim 1 wherein the terpolymer is crosslinked with about 2-8 wt. % of a crosslinking agent based on the total weight of the monomers in the terpolymer.

4. A sunscreen composition according to claim 3 wherein said wt. % is about 4-6 wt. %.

5. A sunscreen composition according to claim 1 wherein said crosslinked terpolymer is neutralized to the degree of about 1 g. of the crosslinked terpolymer with about 2.6 g. of 10% NaOH.

6. A sunscreen composition according to claim 1 wherein said crosslinking agent is 1,7-octadiene or 1,9-decadiene.

7. A sunscreen composition according to claim 1 wherein said alpha-olefin is dodecene or tetradecene.

8. A sunscreen composition according to claim 1 which also includes an emollient.

9. A sunscreen composition according to claim 8 which also includes an additional waterproofing agent.

10. A sunscreen composition according to claim 9 which also includes a germacide and a fragrance.

11. A sunscreen composition according to claim 1 which comprises about 0.5-8 wt. % of the crosslinked, neutralized terpolymer, about 1-7 wt. % of the ultraviolet sunscreening agent, about 1-5 wt. % of an emulsifier, and about 70-95 wt. % of water.

12. A sunscreen composition according to claim 11 which also includes about 1-5 wt. % of an emollient.

13. A sunscreen composition according to claim 12 which also includes about 0.1-5 wt. % of said waterproofing agent.

14. A sunscreen composition according to claim 13 which also includes about 0.5-2 wt. % of a germacide and about 0.1-0.5 wt. % of a fragrance.

* * * * *